US008109951B2

(12) United States Patent
Maschke

(10) Patent No.: US 8,109,951 B2
(45) Date of Patent: Feb. 7, 2012

(54) DEVICE FOR IMPLEMENTING A CUTTING BALLOON INTERVENTION WITH IVUS MONITORING

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 396 days.

(21) Appl. No.: 11/093,452

(22) Filed: Mar. 30, 2005

(65) Prior Publication Data

US 2005/0222596 A1 Oct. 6, 2005

(30) Foreign Application Priority Data

Mar. 31, 2004 (DE) ........................ 10 2004 015 639

(51) Int. Cl.
*A61B 17/22* (2006.01)

(52) U.S. Cl. ........................................... 606/159; 606/7

(58) Field of Classification Search .................. 600/470, 600/466, 467; 604/22, 96.01; 606/159, 191, 606/194, 7; 623/1.1
See application file for complete search history.

(56) References Cited

U.S. PATENT DOCUMENTS 4,465,072 A * 8/1984 Taheri .......................... 606/159
4,646,742 A * 3/1987 Packard et al. ............... 606/194
4,909,252 A * 3/1990 Goldberger .................. 606/194
5,049,124 A * 9/1991 Bales, Jr. ......................... 604/22
5,167,233 A * 12/1992 Eberle et al. .................. 600/470
5,193,546 A 3/1993 Shaknovich
5,196,024 A * 3/1993 Barath .......................... 606/159
5,485,845 A * 1/1996 Verdonk et al. ............... 600/463
5,520,189 A * 5/1996 Malinowski et al. ......... 600/466
5,549,551 A * 8/1996 Peacock et al. .......... 604/103.05
5,699,805 A * 12/1997 Seward et al. ................ 600/459
5,865,801 A 2/1999 Houser
5,906,579 A * 5/1999 Vander Salm et al. ........ 600/424
5,976,107 A * 11/1999 Mertens et al. .......... 604/164.13
6,010,449 A * 1/2000 Selmon et al. ................ 600/117
6,258,052 B1 7/2001 Milo
6,497,711 B1 12/2002 Plaia et al.
6,623,496 B2 * 9/2003 Snow et al. .................. 606/159
2002/0019644 A1 2/2002 Hastings et al.
2002/0077647 A1 6/2002 Snow et al.
2004/0017961 A1 * 1/2004 Petersen et al. ................. 385/12

FOREIGN PATENT DOCUMENTS

EP 0 885 594 B1 12/1998
JP 05505739 T 8/1993
JP 05293176 A 11/1993
WO WO 82/04388 12/1982
WO WO 02/078511 A2 10/2002

OTHER PUBLICATIONS

Peter Barath, Michael C. Fishbein, Sandor Vari, James S. Forrester; "Cutting Balloon: A Novel Approach to Percutaneous Angioplasty"; The American Journal of Cardiology; Nov. 1, 1991; pp. 1249-1252; vol. 68.

(Continued)

*Primary Examiner* — Corrine M McDermott
*Assistant Examiner* — Gregory A Anderson

(57) ABSTRACT

Device for implementing a cutting balloon intervention by means of a "cutting balloon" catheter, at the distal end of which is disposed an inflatable balloon with axially running blades mounted thereon, and which has IVUS monitoring, whereby the cutting balloon catheter is combined with an IVUS catheter to form an integrated module.

7 Claims, 3 Drawing Sheets

VI
1'
3'
7
1a
5
VI

OTHER PUBLICATIONS

Cutting Balloon Ultra$^2$™ Over the Wire Device, Boston Scientific Corporation, [retrieved on Mar. 30, 2005], Retrieved from [online], http://www.bostonscientific.com/med__specialty/deviceCategoryList.jhtml?task=tskCategoryList.jhtml§ionId=4&relld=2,74,11005.

Cutting Balloon Ultra$^2$™ Monorail® Device, Boston Scientific Corporation, [retrieved on Mar. 30, 2005], Retrieved from [online], http://www.bostonscientific.com/med__specialty/deviceCategoryList.jhtml?task=tskCategoryList.jhtml§ionId=4&relld=2,74,11005.

Nakamura, Mamoo et al., "Impact of Deep Vessel Wall Injury on Acute Response and Remodeling of Coronary Artery Segments After Cutting Balloon Angioplasty", The American Journal of Cardiology, Jan. 1, 2003, pp. 6-11, vol. 91.

* cited by examiner 1
2
3
4
5
6
7
8
9
10
11
12
13

1
2
3
4
5
6
7
8
9
10

DEVICE FOR IMPLEMENTING A CUTTING BALLOON INTERVENTION WITH IVUS MONITORING

CROSS REFERENCE TO RELATED APPLICATION

This application claims priority of the German application No. 10 2004 015 639.5 DE filed Mar. 31, 2004, which is incorporated by reference herein in its entirety.

FIELD OF THE INVENTION

The invention relates to a device for implementing a cutting balloon intervention by means of a "cutting balloon" catheter, at the distal end of which is disposed an inflatable balloon with axially running blades mounted thereon, and which has IVUS monitoring.

BACKGROUND OF THE INVENTION

Vascular disease, in particular cardiac infarction, is one of the most common fatal illnesses. It is caused by disease of the coronary arteries (arteriosclerosis), in which the build-up of deposits (arteriosclerotic plaque) causes occlusions in the coronary arteries.

Nowadays, if coronary angiography reveals serious stenoses in the coronary arteries, causing angina pectoris which restricts the patient's capability and/or puts the patient at risk, a PTCA (percutaneous transluminal coronary angioplasty) is carried out in the majority of cases. This is done by dilating the narrowings in the coronary arteries using a so-called "balloon catheter".

The working mechanism of the conventional balloon angioplasty for lumen gain is based both on compression of the plaque and on the rearrangement of the non-compressible plaque constituents, facilitated by dissection of the inner and medial vascular layers, and on the excessive dilatation of the vessel circumference. The compression of large quantities of plaque may result in damage to the inner vascular wall, leading to an increased restenosis rate.

The restenosis rate can be reduced by using a stent in the dilated section of the vessel. Implantation of the stent prevents any modification in vessel structure due to the mechanical restoring force of the stent. A significant disadvantage of the method is the additional process stage and the additional costs for the stent.

The cutting balloon is a special balloon on which are mounted three or four small blades depending on the size of the balloon. These are directed upward when the balloon is inflated and make longitudinal incisions into the vascular deposits or "shave" plaque from the vascular wall, before the coronary artery is dilated by the balloon.

The object of this technique is to minimize or even eliminate the elastic restoring force, in order to achieve a wider vascular diameter following the dilatation. Furthermore, irregular lacerations in the inner vascular wall, which might cause acute obstructions following the balloon inflation procedure, are avoided. Clinical studies show that even hyperplasia (inflammatory response with swelling) of the inner layer following balloon dilatation, can also be reduced. Clinical studies have shown that the restenosis rate can be significantly reduced by using the "cutting balloon".

A device according to the cutting balloon principle is described, for example, in WO 82/04388, "Coronary Cutting and Dilating Instrument" and in WO 02/078511 "Inflatable Medical Device with Combination Cutting Elements and Drug Delivery Conduits". An example of a disclosed product is the Cutting Balloon Ultra from Boston Scientific, Mass., USA.

The interventions described above are implemented using an angiography device under x-ray monitoring by means of contrast media. The drawback of this method is that the coronary arteries are only shown in two dimensions and only the actual stenosis is shown on the x-ray image. During the intervention it is difficult for medical staff to distinguish between plaque and vascular wall. This increases the risk of incisions by the balloon blades being made in the wrong place, or of the incisions being too deep (resulting in "deep vessel wall injury").

The problem is described inter alia in the paper "Impact of Deep Vessel Injury on Acute Response and Remodeling of Coronary Artery Segments After Cutting Balloon Angioplasty", Mamoo Nakamura, The American Journal of Cardiology Vol. 91, Jan. 1, 2003.

The introduction of an IVUS (intravascular ultrasound) catheter into the vessel enhances the imaging information, yet has the disadvantage that a relatively expensive catheter must also be inserted into the patient and must be removed from the vessel before the balloon catheter is inserted. An IVUS system is described, for example, in EP 0 885 594 B1 and in U.S. Pat. No. 5,193,546.

SUMMARY OF THE INVENTION

The object of the invention is therefore to configure a device of the type specified above, to provide an optimum device which is easy to use and which enables the point of intervention to be directly monitored, even during the vessel dilatation if necessary, without the tedious process of changing the various catheters.

This object is achieved according to the invention in that the cutting balloon catheter is combined with an IVUS catheter to form an integrated module, whereby rotating IVUS lines are preferably disposed in the tubular catheter sheath of the cutting balloon catheter alongside the inflation line for the balloon, said rotating IVUS lines leading to an IVUS sensor disposed within a ring-shaped window running around the circumference of the catheter sheath directly behind the cutting balloon, or, alternatively, to an IVUS sensor disposed directly forward of the cutting balloon, whereby said cutting balloon is designed in this case as a ring balloon through which the IVUS lines run.

The embodiment according to the invention provides an integrated module comprising a cutting balloon catheter with an IVUS catheter integrated therein, representing an optimum system for opening up complete vascular stenoses. The great advantage of the solution lies in the reduction in process stages and in the catheters used, and also in the reduction of x-rays applied. The IVUS system images provide important additional medical information with high resolution, particularly at close range over the plaque and the vascular wall. This means that the plaque can be identified, and can be removed by using the cutting balloon in the right location, and the success of the procedure can then be checked immediately without subjecting the patient to unnecessarily high levels of contrast media or x-rays. Furthermore, the risk of damage to the vascular wall is reduced.

In a further embodiment of the invention, provision may be made for the IVUS signal line to be located inside a hollow, flexible drive shaft for the IVUS sensor.

If the IVUS sensor is disposed forward of the "cutting-balloon", the catheter sheath of said cutting balloon should preferably be provided with a tapering, rigid section for mounting of the cutting balloon, in which section the hollow, flexible drive shaft for the distally disposed IVUS sensor is accommodated so as to move freely, so that the rotation of this drive shaft cannot be restrained by the inflation of the balloon, or—for that matter—by any contact pressure on the drive shaft for the IVUS sensor which has been guided through said balloon.

In this embodiment it has also proved expedient for the IVUS sensor to be disposed within a ring-shaped, circumferential window in the hollow, flexible drive shaft.

Instead of a rotating IVUS sensor, according to a further exemplary embodiment of this invention provision can be made for IVUS signal lines to be disposed in the tubular sheath of the cutting balloon catheter alongside the inflation line for the balloon, whereby said IVUS signal lines lead to a sensor array comprising a plurality of ultrasound transducers, said sensor array being integrated in the catheter sheath directly forward of or behind the cutting balloon. The provision of such a circumferential sensor array, in which the individual ultrasound transducers function simultaneously as transmitters and receivers, whereby they are appropriately controlled with staggered timing, means that a rotating IVUS sensor is not required and, of course, that no drive shaft is required to accommodate it. Consequently, the rotating couplings for connecting the corresponding components of the combined catheter to the stationary power supply unit are likewise no longer required.

This arrangement with sensor array is therefore particularly suitable if the IVUS sensor is disposed forward of the cutting balloon, since it is necessary only for IVUS signal lines to be guided through the cutting balloon, which is to be configured in this case, of course, as a ring-shaped balloon, but without any rotating parts having to be disposed or accommodated inside said ring-shaped balloon.

According to a further feature of this invention, the cutting balloon catheter sheath is to be provided with inlet and outlet openings at each end for a contrast medium.

In addition to magnets, which may be disposed in the vicinity of the catheter tip formed by the cutting balloon for the purpose of magnetic navigation in the vessel, provision may also be made for an inflatable and preferably multi-chambered balloon, which is used for fixing the catheter in the vessel and/or for vascular dilatation, to be disposed on the catheter tip formed by the cutting balloon.

Finally, there is also scope within the invention for the device to have a guidewire or guiding catheter running through it.

A typical procedure using a device according to the invention is described below.

A guidewire or guiding catheter is inserted under x-ray monitoring, using contrast media as required, until the target position (stenosis) is reached.

The integrated IVUS catheter with cutting balloon is inserted under x-ray monitoring, using contrast media as required, until the target position is reached.

When the required target position is reached, an irrigation fluid is injected as required and the point at which the plaque is to be removed is observed with high resolution.

The cutting balloon intervention is then carried out gradually on the plaque, whereby it is possible for the progress to be inspected by means of IVUS after each dilatation.

Once the intervention has been completed, the entire vessel section is inspected once again by means of IVUS.

In addition to the combined IVUS catheter with cutting balloon as described above, the device according to the invention comprises a device for connecting the proposed catheter to a user interface for the component of the integrated catheter that is used for plaque ablation. As well as a signal interface unit and a preprocessing stage for the IVUS image data, an image processing and image display unit including image memory is provided. A power supply unit and network interface are of course also available.

The IVUS imaging system can be expanded by the addition of menus to facilitate the quantification of the stenoses to be removed, for example the level of stenosis before and after the intervention. In addition, the user interface may incorporate input options for inputting patient data and data for the catheter parameter via keyboard and/or barcode or a mouse.

BRIEF DESCRIPTION OF THE DRAWINGS

Other advantages, features and details of the invention are explained in the following description of an exemplary embodiment, on the basis of the diagrams in which.

DETAILED DESCRIPTION OF THE INVENTION

Figure 1:
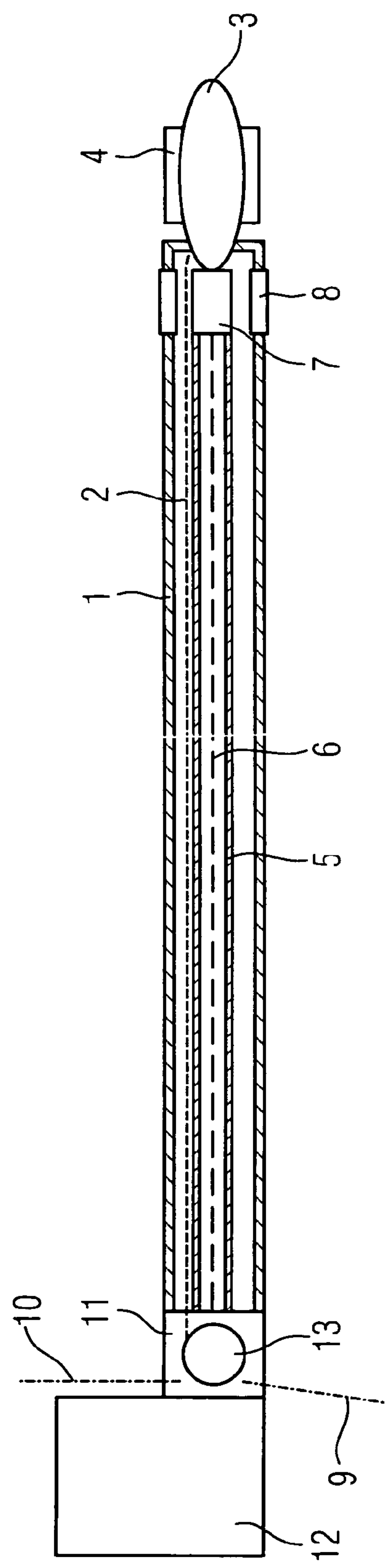
FIG. 1 shows a schematic view of the construction of a combined IVUS catheter with cutting balloon according to the invention, with IVUS sensor disposed directly behind the cutting balloon in its uninflated state to enable the catheter to be inserted.
Figure 2:
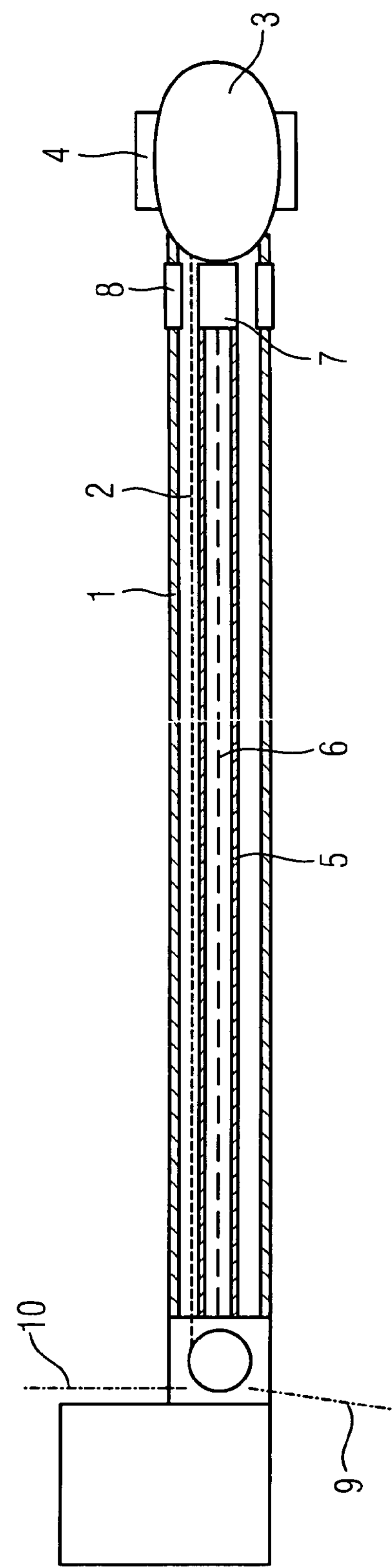
FIG. 2 shows a view, corresponding to FIG. 1, of the combined IVUS catheter with cutting balloon, with the cutting balloon inflated to facilitate the ablation of plaque at an intervention point in a vessel.

On the basis of FIG. 1 and 2 it is possible to identify, in a basic schematic diagram, the construction and functionality of the cutting-balloon catheter with integrated IVUS monitoring to be used for stenosis removal according to the invention. An inflation line 2 for inflating the cutting balloon 3 that is fastened at the distal end of the flexible catheter sheath 1, is disposed within said catheter sheath 1, with a plurality—in particular three or four—of cutting blades 4, being mounted on the outer surface of said cutting balloon and arranged in a manner essentially parallel to the axis. When the balloon is inflated these blades 4 make longitudinal incisions into the vascular deposits, or "shave" plaque from the vascular wall, before the coronary artery is dilated by the balloon.

In addition to the inflation line 2 the flexible catheter sheath 1 also accommodates a hollow flexible drive shaft 5 accommodating an IVUS signal line 6 for an IVUS sensor 7, said IVUS sensor 7 being disposed directly behind the cutting balloon 3 within a ring-shaped, ultrasound-transparent window 8 in the catheter sheath 1. A connection for contrast media and possibly irrigation fluid, which can be pumped through the catheter sheath to an outlet opening (not shown)

in the vicinity of the ring-shaped window 8, is indicated by 9. 10 indicates the connection line for delivery of pressure gas or pressure fluid to the inflation line 2 for the cutting balloon.

The combined IVUS catheter with cutting balloon is connected to the signal interface and the drive unit 12 for the IVUS system via the mechanical connection system 11. This mechanical connection system 11 incorporates a rotating coupling 13 for the connections.

By feeding the pressure medium in via the line 10 and the inflation line 2, the balloon is inflated from the position at insertion according to FIG. 1 to the position shown in FIG. 2, after being advanced to the point of intervention in the vessel, whereby longitudinal sections are first incised into the vascular deposits by the cutting blades 4, before the vessel—in particular a coronary artery—is dilated by the inflating balloon. This causes the plaque to flake off.

Figure 3:
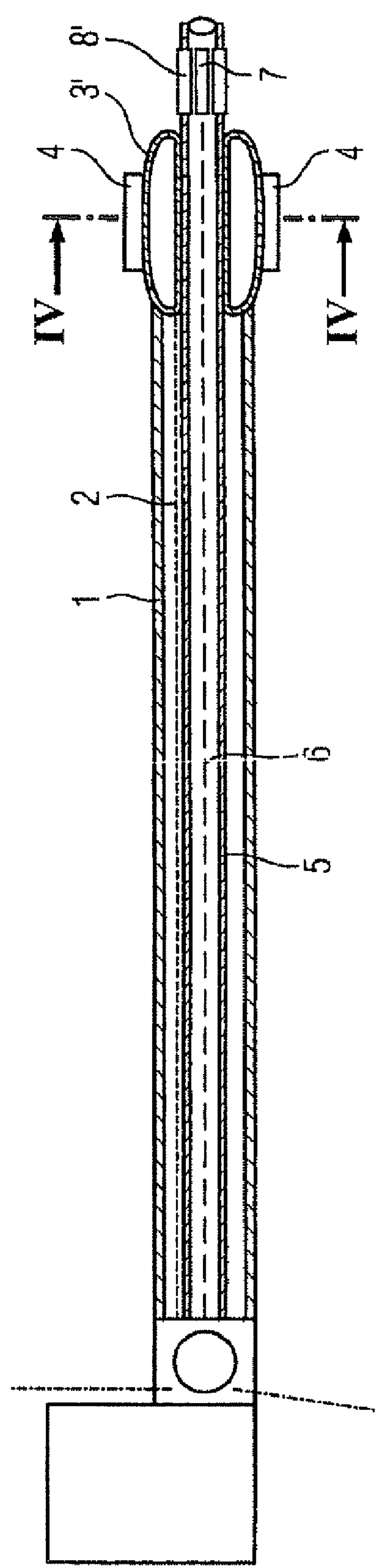
FIG. 3 shows a schematic view, corresponding to FIG. 1, of a second exemplary embodiment of the invention in which the IVUS catheter is running through the cutting balloon and is disposed forward of it.
Figure 4:
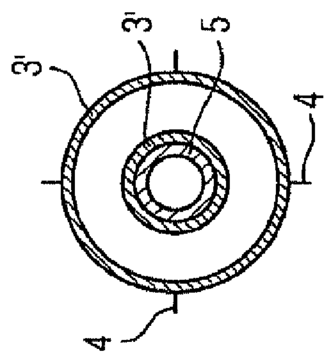
FIG. 4 shows a cross-section along the line IV-IV in FIG. 3.

In the modified exemplary embodiment shown in FIGS. 3 and 4, the IVUS sensor 7 is disposed forward of the cutting balloon 3', which is configured here as a ring-shaped balloon. This means that the hollow, flexible drive shaft 5 for the IVUS sensor 7, with the IVUS signal line 6 disposed therein, runs through the ring-shaped balloon, which—as before—is fastened to the catheter sheath 1. In the embodiment shown, the IVUS sensor is located inside a ring-shaped window 8' in the hollow, flexible drive shaft 5.

Figure 6:
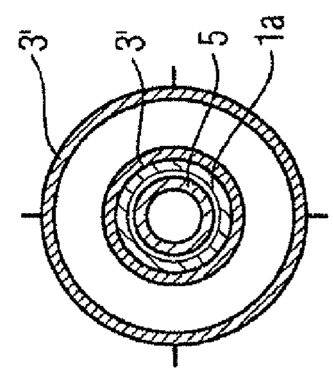
FIG. 6 shows a section along the line VI-VI in FIG. 5.
Figure 5:
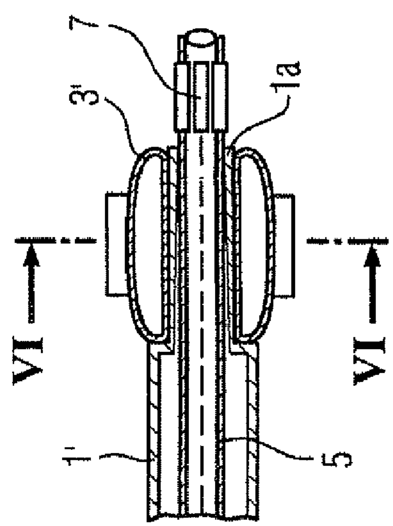
FIG. 5 shows a partial view of a third exemplary embodiment in which the drive shaft for the distally disposed IVUS sensor, and the cutting balloon, are separated from one another by a tapering, rigid section of the catheter sheath.

To reduce the degree by which the rotation of the drive shaft 5 for the IVUS sensor, which runs through this cutting balloon 3', is restricted by the fixed position of the balloon, provision is made in the exemplary embodiment according to FIGS. 5 and 6 (as compared to the exemplary embodiment according to FIGS. 3 and 4) for the cutting balloon 3 not simply to be disposed freely at the distal end of the catheter sheath 1, but on a tapered, rigid section la running through the cutting balloon 3', whereby the hollow, flexible drive shaft 5 for the distally disposed IVUS sensor 7 is accommodated so as to move freely in said tapered, rigid section. As a result, the drive shaft 5 does not move against the inner wall of the ring shaped cutting balloon with correspondingly high friction, but against the rigid section I a of the catheter sheath 1', said rigid section having been designed to ensure low friction, especially since this section cannot be additionally pressed against the drive shaft 5 by the inflation pressure of the cutting balloon, as in the previous exemplary embodiment.

Figure 7:
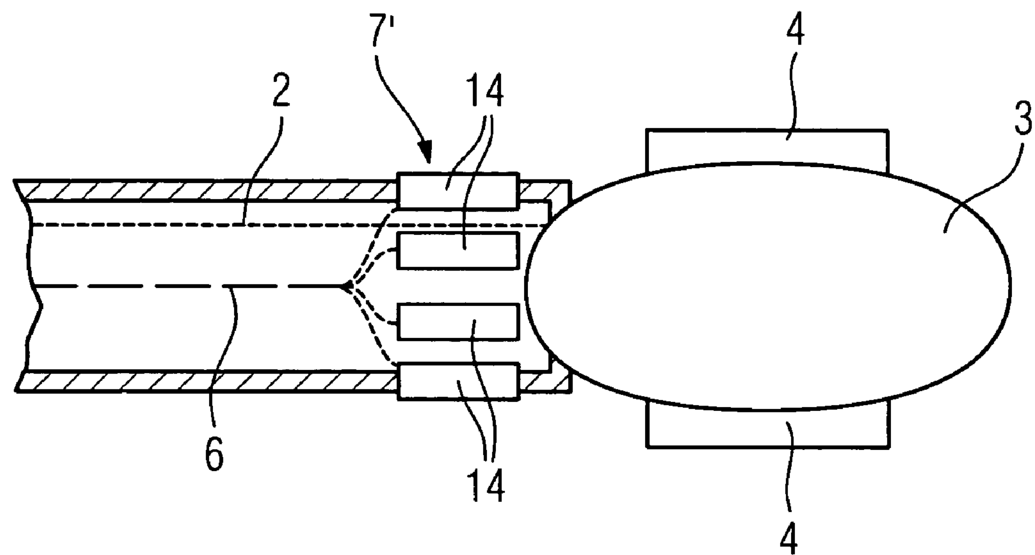
FIG. 7 shows the front section of a fourth exemplary embodiment of an IVUS catheter with cutting balloon according to the invention, with a sensor array instead of a rotating IVUS sensor directly behind the cutting balloon.

The exemplary embodiment according to FIG. 7 essentially differs from that shown in FIGS. 1 to 6 in that no rotating IVUS sensor 7 is provided. Instead, a circumferential sensor array 7' integrated in the catheter sheath 1 and comprising a plurality of ultrasound transducers 14 distributed equidistantly around its circumference, whereby said ultrasound transducers can be controlled, with staggered timing, via the IVUS signal line 6, and can function simultaneously as transmitters and receivers. This use of a sensor array instead of a rotating IVUS sensor means, of course, that the hollow, flexible drive shaft 5 of the previous exemplary embodiments is no longer required.

Figure 8:
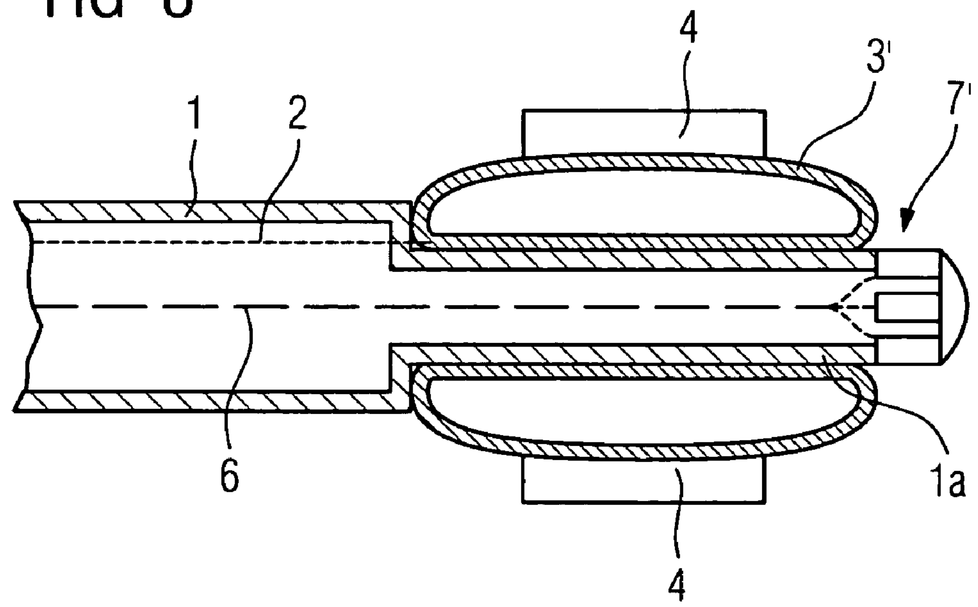
FIG. 8 shows a modified fifth exemplary embodiment of the invention with sensor array disposed forward of the cutting balloon.

This also applies for the embodiment according to FIG. 8, which represents a modification compared to FIG. 7, whereby the IVUS sensor is formed by a sensor array 7' disposed forward of the cutting balloon 3', which, in turn, is configured here as a ring-shaped balloon. This sensor array is disposed at the distal end of the tapered front section 1*a* of the catheter sheath 1, on which, in turn, the ring-shaped cutting balloon 3' is mounted.

The invention is not limited to the exemplary embodiments shown. Thus magnetic navigation would also be possible, with permanent magnets or—alternatively—with electromagnets on the catheter tip or on the catheter, whereby these magnets and their position are not shown in the diagrams. In addition, an inflatable balloon—preferably even with several chambers—could be used in the vicinity of the tip, in order to bring the catheter tip to the required position and keep it there during the intervention, and—if possible—also to be used additionally as a dilatation balloon. This balloon is likewise not shown in the drawings. Furthermore, x-ray markers that are known per se could be provided on the catheter shaft, and also—of course—openings for a guidewire. Finally, it may be noted that the proposed solution of a combined IVUS catheter with cutting balloon for the removal of complete stenoses is not limited to use in coronary arteries, but is essentially suitable for all types of vessels in the body.

The invention claimed is:

1. A device for implementing a cutting balloon intervention, comprising:

an inflatable cutting balloon having axially running blades mounted thereon;

a catheter sheath having a tapered, rigid section extending through the balloon for mounting the cutting balloon thereon;

a hollow, flexible drive shaft disposed within the catheter sheath and extending through the balloon, wherein the drive shaft accommodates a rotating IVUS signal line alongside an inflation line for the balloon;

an IVUS sensor disposed directly forward of the balloon and the rotating IVUS signal line;

wherein the tapered, rigid section accommodates the hollow, flexible drive shaft for the IVUS sensor; and wherein the balloon is mounted directly over a tapered portion of the tapered rigid section such that upon expansion of the balloon, a first end of the tapered portion is in contact with the drive shaft and a second end of the tapered portion is not in contact with the drive shaft to prevent restraint of the drive shaft and to enable the drive shaft to be secured yet move freely within the tapered portion.

2. The device according to claim 1, wherein the balloon is a ring balloon through which the IVUS line extends.

3. The device according to claim 1, wherein the IVUS sensor is disposed within a ring-shaped, circumferential window in the hollow, flexible drive shaft.

4. The device according to claim 1, wherein the catheter sheath is provided with inlet and outlet openings at each end for a contrast medium or an irrigation fluid.

5. The device according to claim 1, wherein magnets are disposed in the vicinity of a tip of the catheter sheath for magnetic navigation in the vessel.

6. The device according to claim 1, wherein an inflatable and multi-chambered balloon is used for fixing the catheter in the vessel and for vascular dilatation and is disposed on a tip of the catheter sheath.

7. The device according to claim 1, wherein the device has a guidewire or guiding catheter extending through it.

* * * * *